(12) United States Patent
Cormier et al.

(10) Patent No.: US 9,155,580 B2
(45) Date of Patent: Oct. 13, 2015

(54) MULTI-THREADED CANNULATED BONE ANCHORS

(75) Inventors: Philip Cormier, Raynham, MA (US); Frank Spratt, Le Locle (CH); Richard Fournier, Raynham, MA (US); Sara Root, Raynham, MA (US); Thibault Chandanson, Le Locle (CH)

(73) Assignee: MEDOS INTERNATIONAL SARL (CH)

( * ) Notice: Subject to any disclaimer, the term of this patent is extended or adjusted under 35 U.S.C. 154(b) by 0 days.

(21) Appl. No.: 13/591,811

(22) Filed: Aug. 22, 2012

(65) Prior Publication Data

US 2013/0053901 A1 Feb. 28, 2013

Related U.S. Application Data

(63) Continuation of application No. 61/527,389, filed on Aug. 25, 2011.

(51) Int. Cl.
*A61B 17/70* (2006.01)
*A61B 17/86* (2006.01)

(52) U.S. Cl.
CPC .............. *A61B 17/863* (2013.01); *A61B 17/864* (2013.01); *A61B 17/8635* (2013.01); *A61B 17/7032* (2013.01); *A61B 17/7037* (2013.01)

(58) Field of Classification Search
CPC ........... A61B 17/7032; A61B 17/7037; A61B 17/8605; A61B 17/864; A61B 17/863; A61B 17/8625; A61B 17/8685; A61B 17/8635
USPC .................................. 606/264–275, 301–321
See application file for complete search history.

(56) References Cited

U.S. PATENT DOCUMENTS

| | | | |
|---|---|---|---|
| 3,987,499 A | 10/1976 | Scharbach |
| 4,611,581 A | 9/1986 | Steffee |
| 4,653,489 A | 3/1987 | Tronzo |
| 4,950,270 A | 8/1990 | Bowman |
| 5,019,079 A | 5/1991 | Ross |

(Continued)

FOREIGN PATENT DOCUMENTS

| | | |
|---|---|---|
| EP | 0340159 | 11/1989 |
| EP | 0716832 | 6/1996 |

(Continued)

OTHER PUBLICATIONS

Confidence Spinal Cement System Brochure, 2008, 6 pages.
(Continued)

*Primary Examiner* — Michael T Schaper
*Assistant Examiner* — Amy Sipp
(74) *Attorney, Agent, or Firm* — David A. Lane, Jr.

(57) ABSTRACT

A cannulated bone anchor assembly includes a bone anchor, a receiver member for receiving a spinal fixation element to be coupled to the bone anchor, and a closure mechanism to fix the spinal fixation element with respect to the receiver member. The bone anchor includes a distal shaft having a first threaded section distal to a proximal head, a second threaded section distal to and adjacent the first threaded section, and a third threaded section distal to and adjacent the second threaded section. The first threaded section having a constant major and minor diameter. The second threaded section having a tapering major and minor diameter. The third threaded section having a tapering major diameter and a constant minor diameter.

12 Claims, 5 Drawing Sheets

(56) References Cited

U.S. PATENT DOCUMENTS

| | | | |
|---|---|---|---|
| 5,034,011 A | 7/1991 | Howland | |
| 5,047,030 A | 9/1991 | Draenert | |
| 5,084,050 A | 1/1992 | Draenert | |
| 5,098,435 A | 3/1992 | Stednitz | |
| 5,169,400 A | 12/1992 | Muhling | |
| 5,180,382 A | 1/1993 | Frigg et al. | |
| 5,192,282 A | 3/1993 | Draenert | |
| 5,209,753 A * | 5/1993 | Biedermann et al. | 606/304 |
| 5,435,723 A * | 7/1995 | O'Brien | 433/174 |
| 5,456,685 A | 10/1995 | Huebner | |
| 5,492,442 A | 2/1996 | Lasner | |
| 5,514,137 A | 5/1996 | Coutts | |
| 5,562,672 A | 10/1996 | Huebner et al. | |
| 5,593,410 A | 1/1997 | Vrespa | |
| 5,601,553 A | 2/1997 | Trebing et al. | |
| 5,658,338 A | 8/1997 | Tullos | |
| 5,695,497 A | 12/1997 | Stahelin | |
| 5,697,917 A | 12/1997 | Sadowski | |
| 5,698,497 A | 12/1997 | Haddon | |
| 5,713,903 A | 2/1998 | Sander et al. | |
| 5,725,581 A | 3/1998 | Branemark | |
| 5,735,898 A | 4/1998 | Brånemark | |
| 5,738,685 A | 4/1998 | Halm et al. | |
| 5,743,912 A | 4/1998 | Lahille | |
| 5,816,812 A * | 10/1998 | Kownacki et al. | 433/174 |
| 5,824,087 A | 10/1998 | Aspden | |
| 5,964,768 A | 10/1999 | Huebner | |
| 5,997,539 A | 12/1999 | Errico et al. | |
| 6,010,508 A | 1/2000 | Bradley | |
| 6,030,162 A * | 2/2000 | Huebner | 411/413 |
| 6,048,343 A | 4/2000 | Mathis | |
| 6,074,393 A | 6/2000 | Sitoto | |
| 6,083,225 A | 7/2000 | Winslow | |
| 6,083,227 A | 7/2000 | Saurat et al. | |
| 6,096,060 A * | 8/2000 | Fitts et al. | 606/232 |
| 6,117,137 A | 9/2000 | Halm et al. | |
| 6,214,012 B1 | 4/2001 | Karpman | |
| 6,217,581 B1 | 4/2001 | Tolson | |
| 6,267,785 B1 | 7/2001 | Masini | |
| 6,283,973 B1 | 9/2001 | Hubbard | |
| 6,348,055 B1 | 2/2002 | Preissman | |
| 6,355,043 B1 | 3/2002 | Adam | |
| 6,375,657 B1 | 4/2002 | Doubler et al. | |
| 6,375,659 B1 | 4/2002 | Erbe | |
| 6,383,190 B1 | 5/2002 | Preissman | |
| 6,402,758 B1 | 6/2002 | Tolson | |
| 6,436,100 B1 | 8/2002 | Berger | |
| 6,517,542 B1 | 2/2003 | Papay | |
| 6,551,323 B2 | 4/2003 | Doubler et al. | |
| 6,554,830 B1 | 4/2003 | Chappius | |
| 6,565,566 B1 | 5/2003 | Wagner et al. | |
| 6,565,572 B2 | 5/2003 | Chappius | |
| 6,565,573 B1 | 5/2003 | Ferrante et al. | |
| 6,575,976 B2 | 6/2003 | Grafton | |
| 6,582,439 B1 | 6/2003 | Sproul | |
| 6,585,740 B2 * | 7/2003 | Schlapfer et al. | 606/308 |
| 6,589,245 B1 | 7/2003 | Weiler | |
| 6,620,169 B1 | 9/2003 | Peterson | |
| 6,645,213 B2 | 11/2003 | Sand | |
| 6,648,893 B2 | 11/2003 | Dudasik | |
| 6,676,664 B1 | 1/2004 | Al-Assir | |
| 6,679,890 B2 | 1/2004 | Margulies | |
| 6,689,137 B2 | 2/2004 | Reed | |
| 6,719,761 B1 | 4/2004 | Reiley | |
| 6,752,809 B2 | 6/2004 | Gorek | |
| 6,755,829 B1 | 6/2004 | Bono et al. | |
| 6,755,835 B2 | 6/2004 | Schultheiss | |
| 6,800,078 B2 | 10/2004 | Reed | |
| 6,800,079 B2 | 10/2004 | Reed | |
| 6,824,564 B2 | 11/2004 | Crozet | |
| 6,846,313 B1 | 1/2005 | Rogers et al. | |
| 6,863,671 B1 | 3/2005 | Strobel et al. | |
| 6,942,666 B2 | 9/2005 | Overaker et al. | |
| 6,981,973 B2 | 1/2006 | McKinley | |
| 6,981,974 B2 | 1/2006 | Berger | |
| 7,097,648 B1 | 8/2006 | Globerman | |
| 7,112,205 B2 | 9/2006 | Carrison | |
| 7,179,261 B2 | 2/2007 | Sicvol | |
| 7,186,255 B2 * | 3/2007 | Baynham et al. | 606/266 |
| 7,235,079 B2 | 6/2007 | Jensen | |
| 7,250,055 B1 | 7/2007 | Vanderwalle | |
| 7,261,716 B2 | 8/2007 | Strobel | |
| 7,300,439 B2 | 11/2007 | May | |
| 7,309,346 B2 | 12/2007 | Martinek | |
| 7,325,470 B2 | 2/2008 | Kay et al. | |
| 7,354,442 B2 | 4/2008 | Sasso et al. | |
| 7,455,685 B2 | 11/2008 | Justis | |
| 7,527,638 B2 | 5/2009 | Anderson | |
| 7,544,196 B2 | 6/2009 | Bagga | |
| 7,572,263 B2 | 8/2009 | Preissman | |
| 7,608,097 B2 | 10/2009 | Kyle | |
| 7,621,950 B1 | 11/2009 | Globerman | |
| 7,766,945 B2 | 8/2010 | Nilsson et al. | |
| 7,799,062 B2 | 9/2010 | Crozet | |
| 7,824,044 B2 | 11/2010 | Tochigi | |
| 7,824,411 B2 | 11/2010 | Varieur | |
| 7,824,413 B2 | 11/2010 | Varieur | |
| 7,850,717 B2 * | 12/2010 | Dewey et al. | 606/246 |
| 7,935,138 B1 | 5/2011 | Richelsoph | |
| 8,012,186 B2 * | 9/2011 | Pham et al. | 606/265 |
| 8,075,604 B2 | 12/2011 | Denis et al. | |
| 8,147,500 B2 | 4/2012 | Beyar | |
| 8,231,632 B1 * | 7/2012 | Jordan et al. | 606/92 |
| 8,257,399 B2 * | 9/2012 | Biedermann et al. | 606/265 |
| 8,277,494 B2 * | 10/2012 | Biedermann et al. | 606/301 |
| 8,308,782 B2 * | 11/2012 | Jackson | 606/308 |
| 8,343,201 B2 * | 1/2013 | Biyani et al. | 606/318 |
| 8,366,717 B1 * | 2/2013 | Jordan et al. | 606/94 |
| 8,382,811 B2 * | 2/2013 | Crook et al. | 606/315 |
| 8,403,973 B2 * | 3/2013 | Biyani et al. | 606/318 |
| 8,491,302 B2 * | 7/2013 | Arni | 433/173 |
| 8,690,930 B2 * | 4/2014 | Biedermann et al. | 606/304 |
| 8,758,012 B2 * | 6/2014 | Hurson | 433/173 |
| 2001/0004710 A1 | 6/2001 | Felt | |
| 2001/0007074 A1 | 7/2001 | Strobel | |
| 2001/0021852 A1 | 9/2001 | Chappius | |
| 2002/0038123 A1 | 3/2002 | Visotsky | |
| 2002/0049447 A1 | 4/2002 | Li | |
| 2002/0082605 A1 | 6/2002 | Reiley | |
| 2002/0123752 A1 | 9/2002 | Schultheiss | |
| 2002/0147454 A1 | 10/2002 | Neto | |
| 2002/0169453 A1 | 11/2002 | Berger | |
| 2002/0193799 A1 | 12/2002 | Chappuis | |
| 2003/0045881 A1 | 3/2003 | Barouk | |
| 2003/0045885 A1 | 3/2003 | Margulies | |
| 2003/0078589 A1 | 4/2003 | Preissman | |
| 2003/0083662 A1 | 5/2003 | Middleton | |
| 2003/0105468 A1 | 6/2003 | Gorek | |
| 2003/0120277 A1 | 6/2003 | Berger | |
| 2003/0130741 A1 | 7/2003 | McMinn | |
| 2004/0006346 A1 | 1/2004 | Holmen | |
| 2004/0006348 A1 | 1/2004 | Peterson | |
| 2004/0015172 A1 | 1/2004 | Biedermann | |
| 2004/0092946 A1 | 5/2004 | Bagga | |
| 2004/0122431 A1 | 6/2004 | Biedermann | |
| 2004/0176767 A1 | 9/2004 | Bickley | |
| 2004/0210297 A1 | 10/2004 | Lin | |
| 2004/0225292 A1 | 11/2004 | Sasso | |
| 2004/0243137 A1 | 12/2004 | Gorek | |
| 2004/0260303 A1 | 12/2004 | Carrison | |
| 2004/0267265 A1 | 12/2004 | Kyle | |
| 2005/0033303 A1 | 2/2005 | Chappuis | |
| 2005/0033427 A1 | 2/2005 | Freilich | |
| 2005/0038438 A1 * | 2/2005 | Anderson et al. | 606/73 |
| 2005/0055026 A1 | 3/2005 | Biedermann | |
| 2005/0055030 A1 | 3/2005 | Falahee | |
| 2005/0059972 A1 | 3/2005 | Biscup | |
| 2005/0065526 A1 | 3/2005 | Drew et al. | |
| 2005/0070907 A1 | 3/2005 | Abernathie | |
| 2005/0070915 A1 | 3/2005 | Mazzuca | |
| 2005/0101961 A1 * | 5/2005 | Huebner et al. | 606/72 |
| 2005/0107800 A1 | 5/2005 | Frankel et al. | |
| 2005/0137596 A1 | 6/2005 | Uwaydah | |
| 2005/0143823 A1 | 6/2005 | Boyd | |

(56) References Cited

U.S. PATENT DOCUMENTS

| | | |
|---|---|---|
| 2005/0187555 A1 | 8/2005 | Biedermann |
| 2005/0228388 A1 | 10/2005 | Brodke |
| 2005/0240188 A1 | 10/2005 | Chow |
| 2006/0052794 A1 | 3/2006 | McGill |
| 2006/0074421 A1 | 4/2006 | Bickley et al. |
| 2006/0079905 A1 | 4/2006 | Beyar |
| 2006/0095040 A1* | 5/2006 | Schlienger et al. ............. 606/73 |
| 2006/0106390 A1 | 5/2006 | Jensen et al. |
| 2006/0149258 A1 | 7/2006 | Sousa |
| 2006/0149260 A1 | 7/2006 | Lin |
| 2006/0149263 A1* | 7/2006 | Newcomb et al. .............. 606/73 |
| 2006/0235410 A1 | 10/2006 | Ralph et al. |
| 2006/0264967 A1 | 11/2006 | Ferreyro |
| 2006/0271047 A1 | 11/2006 | Jackson |
| 2006/0271054 A1 | 11/2006 | Sucec |
| 2007/0027230 A1 | 2/2007 | Beyar |
| 2007/0032567 A1 | 2/2007 | Beyar |
| 2007/0053765 A1 | 3/2007 | Warnick et al. |
| 2007/0066987 A1* | 3/2007 | Scanlan et al. ................ 606/184 |
| 2007/0093818 A1* | 4/2007 | Biedermann et al. ........... 606/61 |
| 2007/0161985 A1 | 7/2007 | Demakas et al. |
| 2007/0233122 A1 | 10/2007 | Denis et al. |
| 2007/0233260 A1* | 10/2007 | Cragg ........................ 623/17.12 |
| 2007/0248054 A1 | 10/2007 | Chen |
| 2007/0260261 A1 | 11/2007 | Runco |
| 2008/0020344 A1 | 1/2008 | Hansson |
| 2008/0065083 A1 | 3/2008 | Truckai |
| 2008/0132956 A1* | 6/2008 | Biedermann et al. ......... 606/300 |
| 2008/0132957 A1* | 6/2008 | Matthis et al. ................ 606/301 |
| 2008/0140132 A1 | 6/2008 | Perez-Cruet |
| 2008/0140136 A1 | 6/2008 | Jackson |
| 2008/0154314 A1 | 6/2008 | McDevitt |
| 2008/0154315 A1 | 6/2008 | Jackson |
| 2008/0161864 A1 | 7/2008 | Beck et al. |
| 2008/0177331 A1 | 7/2008 | Perez-Cruet et al. |
| 2008/0177335 A1 | 7/2008 | Melkent |
| 2008/0188898 A1 | 8/2008 | Jackson |
| 2008/0200915 A1 | 8/2008 | Globerman |
| 2008/0212405 A1 | 9/2008 | Globerman |
| 2008/0221623 A1 | 9/2008 | Gooch |
| 2008/0221624 A1 | 9/2008 | Gooch |
| 2008/0228192 A1 | 9/2008 | Beyar |
| 2008/0234744 A1 | 9/2008 | Zylber |
| 2008/0234756 A1 | 9/2008 | Sutcliffe et al. |
| 2008/0234761 A1 | 9/2008 | Jackson |
| 2008/0249530 A1 | 10/2008 | Truckai |
| 2008/0287994 A1 | 11/2008 | Perez-Cruet et al. |
| 2008/0300639 A1 | 12/2008 | Martin |
| 2009/0012525 A1* | 1/2009 | Buehlmann et al. ............ 606/92 |
| 2009/0062868 A1* | 3/2009 | Casutt ........................... 606/316 |
| 2009/0131867 A1* | 5/2009 | Liu et al. .................... 604/96.01 |
| 2009/0163956 A1* | 6/2009 | Biedermann et al. ......... 606/265 |
| 2009/0198291 A1 | 8/2009 | Kevin et al. |
| 2009/0248088 A1* | 10/2009 | Biedermann ................. 606/305 |
| 2009/0264892 A1 | 10/2009 | Beyar |
| 2009/0264942 A1 | 10/2009 | Beyar |
| 2010/0004692 A1* | 1/2010 | Biedermann et al. ......... 606/305 |
| 2010/0023017 A1 | 1/2010 | Beyar |
| 2010/0030135 A1 | 2/2010 | Mitchell |
| 2010/0076503 A1* | 3/2010 | Beyar et al. .................. 606/86 R |
| 2010/0094352 A1* | 4/2010 | Iott et al. ....................... 606/301 |
| 2010/0114174 A1 | 5/2010 | Jones |
| 2010/0137918 A1 | 6/2010 | Wilcox et al. |
| 2010/0152785 A1* | 6/2010 | Forton et al. .................. 606/301 |
| 2010/0234904 A1 | 9/2010 | Richelsoph |
| 2010/0256681 A1 | 10/2010 | Hammer et al. |
| 2010/0274295 A1 | 10/2010 | Carls et al. |
| 2010/0318136 A1* | 12/2010 | Jackson et al. ................ 606/305 |
| 2011/0093021 A1 | 4/2011 | Fanger et al. |
| 2011/0125199 A1 | 5/2011 | Griffin |
| 2011/0125265 A1* | 5/2011 | Bagga et al. ................ 623/16.11 |
| 2011/0137355 A1 | 6/2011 | Rinner |
| 2011/0152948 A1 | 6/2011 | Crook et al. |
| 2011/0257690 A1* | 10/2011 | Rezach ........................ 606/302 |
| 2011/0288599 A1 | 11/2011 | Michielli et al. |
| 2012/0130433 A1* | 5/2012 | Huebner ....................... 606/300 |
| 2013/0053901 A1 | 2/2013 | Cormier |
| 2013/0085536 A1* | 4/2013 | Biedermann et al. ......... 606/308 |
| 2013/0211468 A1* | 8/2013 | Huebner ....................... 606/328 |

FOREIGN PATENT DOCUMENTS

| | | |
|---|---|---|
| EP | 1405607 | 4/2004 |
| EP | 1430846 | 6/2004 |
| EP | 1835859 | 7/2006 |
| EP | 1769777 | 4/2007 |
| EP | 1991145 | 11/2008 |
| EP | 1491156 | 12/2008 |
| JP | 2009-240776 | 10/2009 |
| WO | WO 98/48738 | 11/1998 |
| WO | WO 2004/032774 | 4/2004 |
| WO | WO 2004/100808 | 11/2004 |
| WO | WO 2005/087120 | 9/2005 |
| WO | WO 2006/070961 | 7/2006 |
| WO | WO 2007/036815 | 9/2007 |
| WO | WO 2007/122608 | 4/2009 |
| WO | WO 2010/148299 | 12/2010 |

OTHER PUBLICATIONS

Confidence Surgical Technique Guide Spinal Cement System.
International Search Report re: PCT/US2012/052045 dated Nov. 2, 2012.
International Search Report re: PCT/US2011/036966 dated Sep. 14, 2011.

* cited by examiner

FIG. 1
FIG. 2
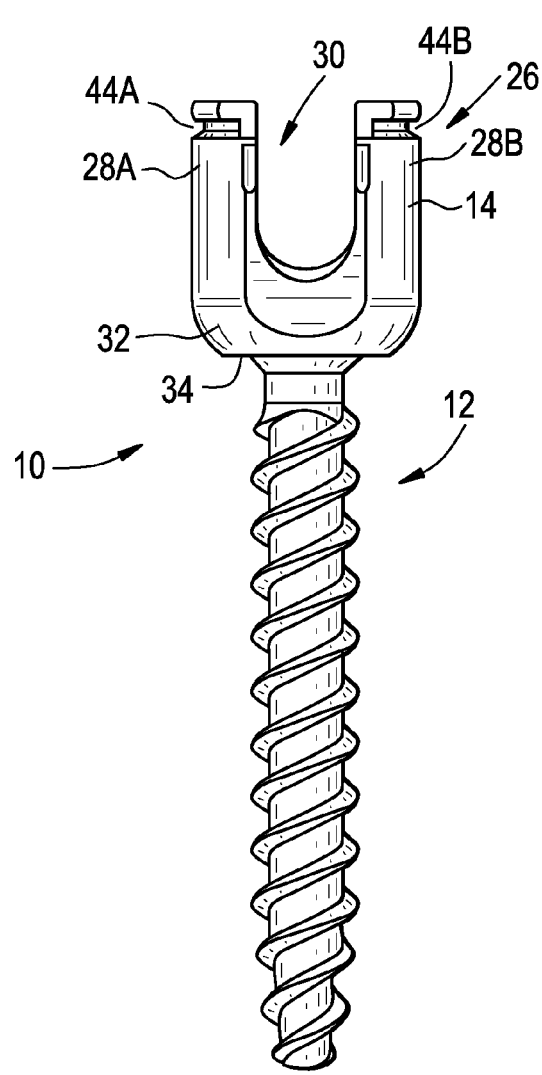
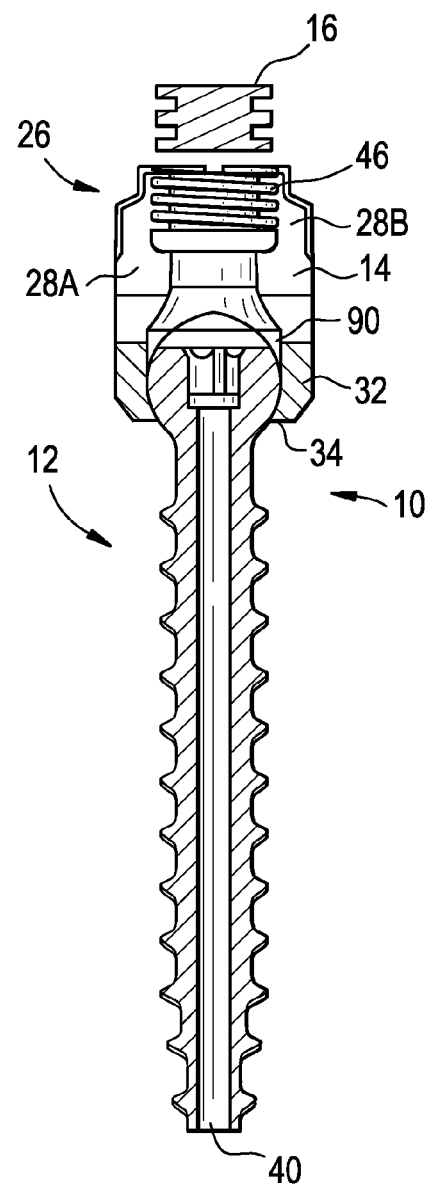

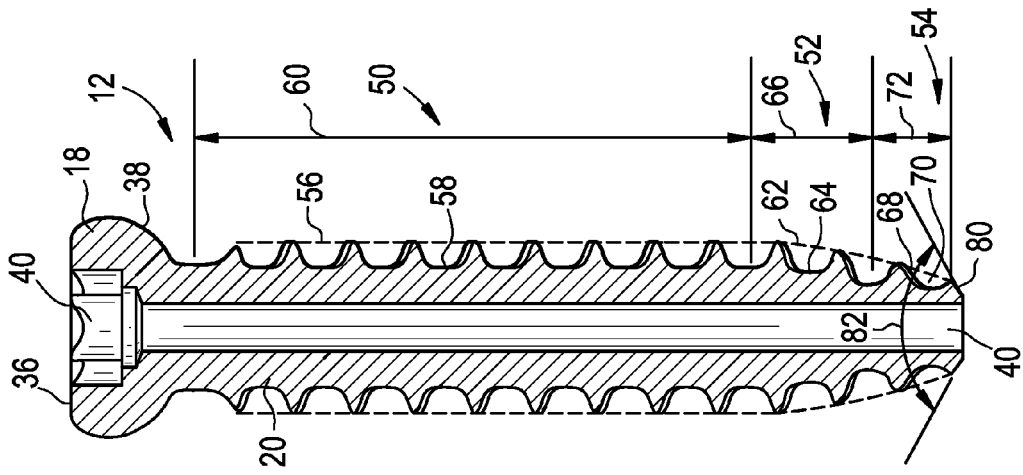
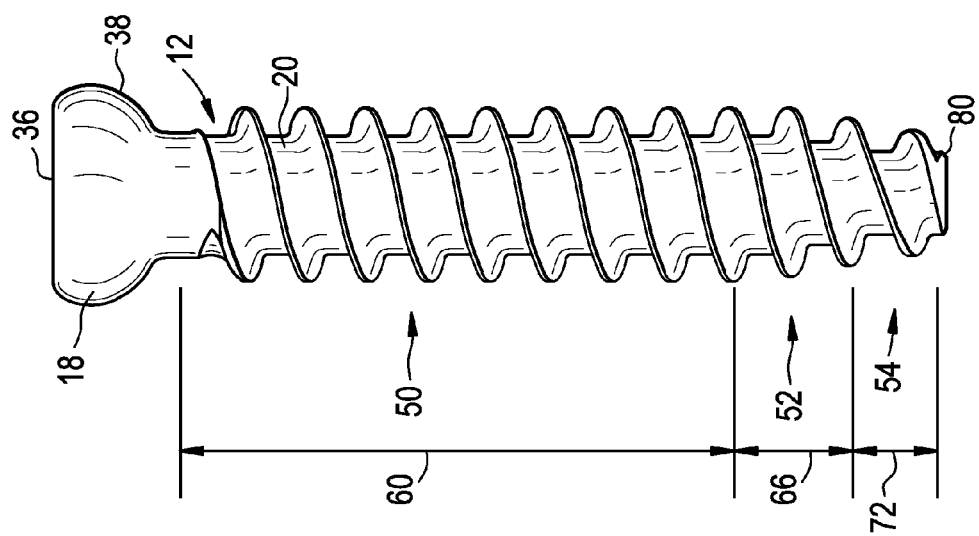

FIG. 5
FIG. 6
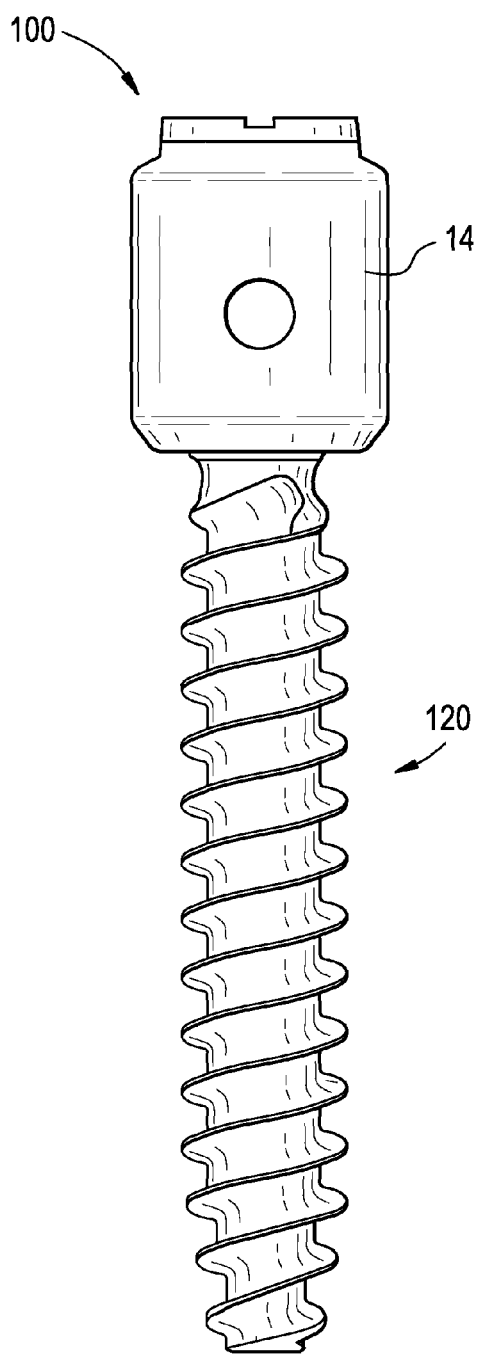
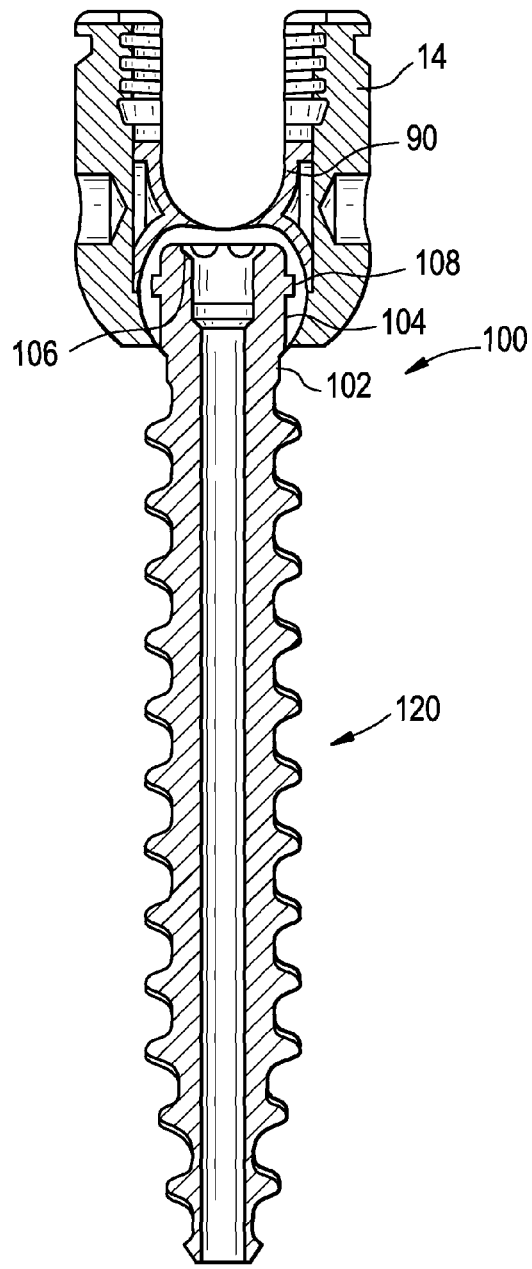

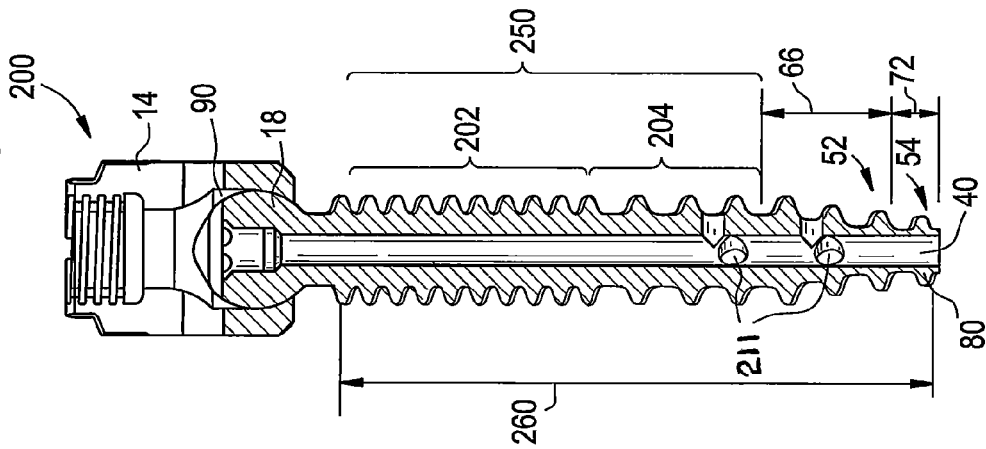
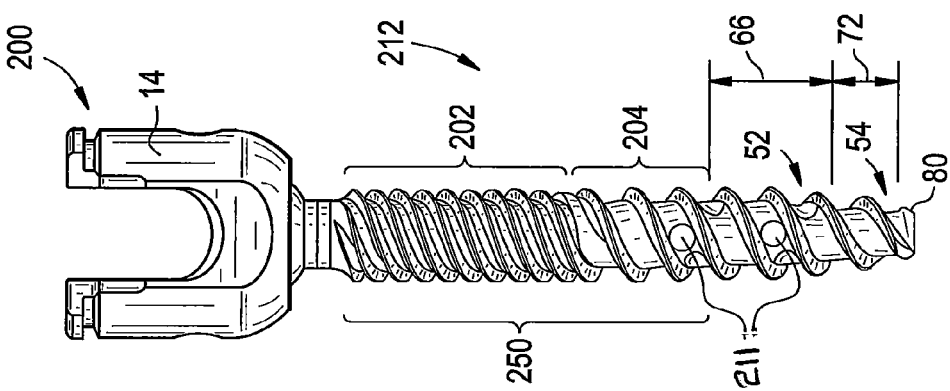
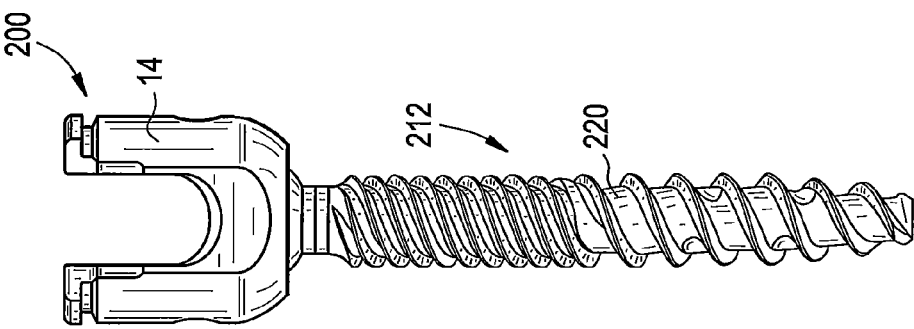

MULTI-THREADED CANNULATED BONE ANCHORS

REFERENCE TO RELATED APPLICATION

This application claims the benefit of U.S. Provisional Application No. 61/527,389, filed Aug. 25, 2011, which is incorporated herein by reference.

BACKGROUND

Bone anchors may be used in orthopedic surgery to fix bone during the healing or fusion process. In spinal surgery, bone anchors may be used with spinal fixation elements, such as spinal rods, to stabilize multiple vertebrae either rigidly, in which no relative motion between the vertebrae is desired, and dynamically, in which limited, controlled motion between the vertebrae is desired. In certain procedures, such as minimally invasive procedures, it may be desirable to deliver the bone anchor to the vertebra over a guide wire or other guidance instrument. To facilitate this, bone anchors may be cannulated, i.e., may have a central passage through the bone anchor that is sized to receive the guide wire. One problem with the use of cannulated bone anchors is that when such bone anchors are used in a procedure without a guide wire, for example, in an open or non-minimally invasive procedure, it may be difficult to start the bone anchor in the proximal surface of the bone unless either an opening in the bone is pre-threaded using a tap or other instrument or the surgeon applies a significant distal force on the bone anchor. Accordingly, there is need for improved cannulated bone anchors that facilitate placement of the anchor in the bone.

SUMMARY

Disclosed herein are improved bone anchor assemblies and, in particular, improved bone anchor assemblies used in connection with spinal fixation elements to fix multiple vertebrae either rigidly or dynamically.

In accordance with one aspect, a bone anchor assembly may include a a bone anchor, a receiver member for receiving a spinal fixation element to be coupled to the bone anchor, and a closure mechanism to fix the spinal fixation element with respect to the receiver member. The bone anchor may include a distal shaft having a first threaded section distal to a proximal head, a second threaded section distal to and adjacent the first threaded section, and a third threaded section distal to and adjacent the second threaded section. The first threaded section may have a constant major and minor diameter. The second threaded section may have a tapering major and minor diameter. The third threaded section may have a tapering major diameter and a constant minor diameter. The bone anchor may include a central passage extending from the proximal head through the distal shaft.

BRIEF DESCRIPTION OF THE FIGURES

These and other features and advantages of the devices and methods disclosed herein will be more fully understood by reference to the following detailed description in conjunction with the attached drawings in which like reference numerals refer to like elements through the different views. The drawings illustrate principles of the devices and methods disclosed herein and, although not to scale, show relative dimensions.

FIG. 1 is a side view of an exemplary embodiment of a bone anchor assembly;

FIG. 2 is a side view in cross section of the bone anchor assembly of FIG. 1;

FIG. 3 is a side view of the bone anchor of the bone anchor assembly of FIG. 1;

FIG. 4 is a side view in cross section of the bone anchor of the bone anchor assembly FIG. 1;

FIG. 5 is a side view of another exemplary embodiment of a bone anchor assembly;

FIG. 6 is a side view in cross section of the bone anchor assembly FIG. 5;

FIG. 8 is a side view of another exemplary embodiment of a bone anchor assembly;

FIG. 9 is a side view of the bone anchor assembly FIG. 8, illustrating the bone anchor rotated 90° from FIG. 8; and FIG. 10 is a side view in cross section of the bone anchor assembly FIG. 8.

DETAIL DESCRIPTION OF EXEMPLARY EMBODIMENTS

Figure 7:
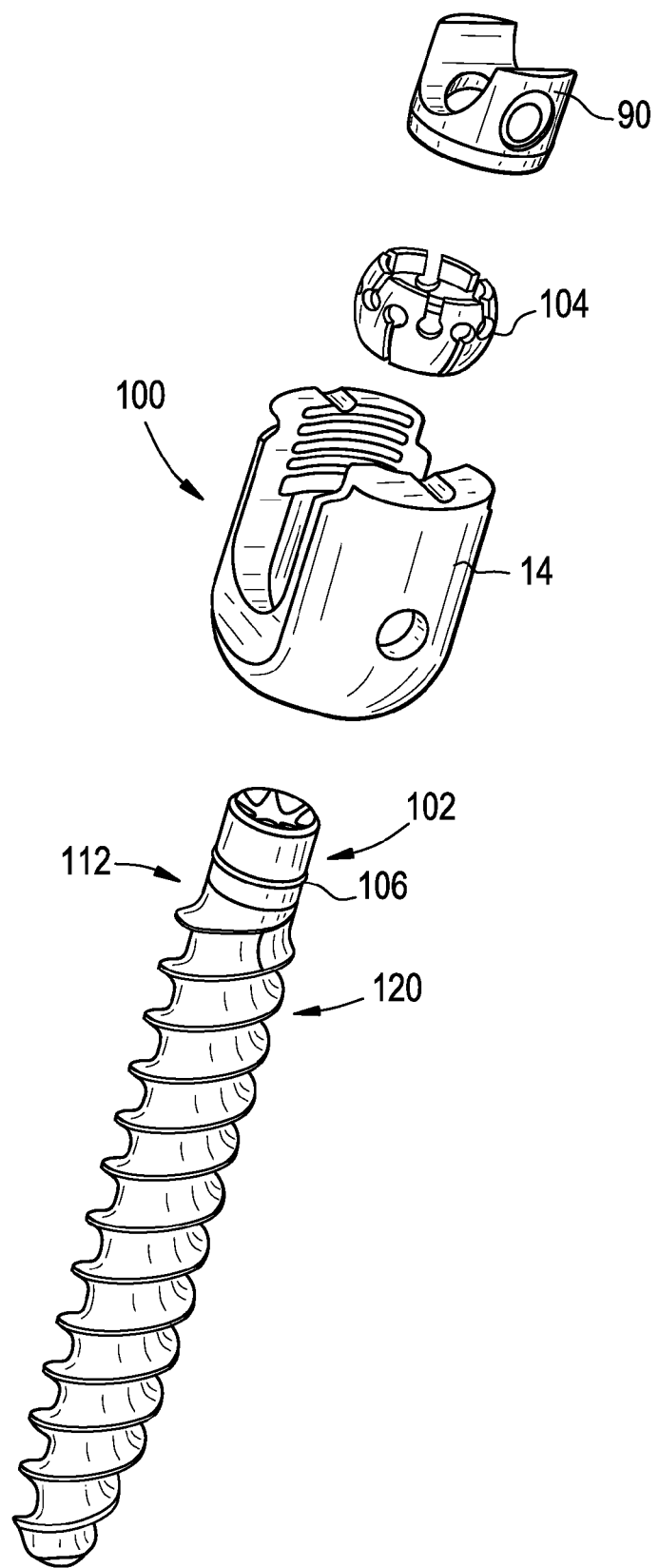
FIG. 7 is an exploded view of the bone anchor assembly FIG. 5.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-4 illustrate an exemplary embodiment of a bone anchor assembly 10 including a bone anchor 12, a receiver member 14 for receiving a spinal fixation element, such as a spinal rod, to be coupled to the bone anchor 12, and a closure mechanism 16 to capture a spinal fixation element within the receiver member 14 and fix the spinal fixation element with respect to the receiver member 14. The bone anchor 12 includes a proximal head 18 and a distal shaft 20 configured to engage bone. The receiver member 14 has a proximal end 26 having a pair of spaced apart arms 28A, 28B defining a recess 30 therebetween and a distal end 32 having a distal end surface 34 defining opening through which at least a portion of the bone anchor 12 extends. The closure mechanism 16 may be positionable between and may engage the arms 28A, 28B to capture a spinal fixation element within the receiver member 14 and fix the spinal fixation element with respect to the receiver member 14.

Continuing to refer to FIGS. 1-4, the proximal head 18 of the bone anchor 12 in the exemplary embodiment is generally in the shape of a truncated sphere having a planar proximal surface 36 and an approximately spherically shaped distal surface 38. The exemplary bone anchor assembly is a polyaxial bone screw designed for posterior implantation in the pedicle or lateral mass of a vertebra. In this regards, the proximal head 18 of the bone anchor 12 engages the distal end 32 of the receiver member 14 in a ball and socket like arrangement in which the proximal head 18, and thus the distal shaft 20, can pivot relative to the receiver member 14. The distal surface 38 of the proximal head 18 of the bone anchor 12 and the mating surface within the distal end 32 of the receiver member 14 may have any shape that facilitates this ball and socket like arrangement, including, for example, spherical (as illustrated), toroidal, conical, frustoconical, and any combinations of these shapes.

The distal shaft 20 of the bone anchor 12 may be cannulated, having a central passage or cannula 40 extending the length of the bone anchor 12 to facilitate delivery of the bone anchor 12 over a guide wire in, for example, minimally invasive procedures. The other components of the bone anchor assembly, including the closure member 16, the receiver member 14, and the compression member 90 (discussed below) may be cannulated or otherwise have an opening to permit the respective component to be delivered over a guide wire.

Continuing to refer to FIGS. 1-4, the proximal end 26 of the receiver member 14 of the exemplary bone anchor assembly 10 includes a pair of spaced apart arms 28A, 28B defining the U-shaped recess 30 therebetween for receiving a spinal fixation element. The distal end 32 of the receiver member 14 is generally cylindrical in shape and includes distal end surface 34 which is generally annular in shape defining a circular opening through which at least a portion of the bone anchor 12 extends. For example, the distal shaft 20 of the bone anchor 12 may extend through the opening. Each arm 28A, 28B of the proximal end 26 of the receiver member 14 extends from the distal end 32 of the receiver member 14 to a free end. The outer surface of each arm 28A, 28B may include a feature, such as a recess, dimple, notch, projection, or the like, to facilitate connection of the receiver member 14 and, thus, the bone anchor assembly 10, to instruments. In the exemplary embodiment, for example, the outer surface of each arm 28A, 28B includes an arcuate groove 44A, 44B at the respective free end of the arms. Such grooves are described in more detail in U.S. Pat. No. 7,179,261, which is incorporated herein by reference.

The proximal end 26 of the receiving member 14 may be configured to receive a closure mechanism, such as internal set screw (closure mechanism 16) or an external cap or nut. For example, the interior surface of each arm 28A, 28B may include a feature, such as a recess, dimple, notch, projection, thread or the like, to facilitate connection of the closure mechanism 16 to the receiver member 14. In the exemplary embodiment, for example, the interior surface of each arm 28A, 28B includes an internal thread 46 on the interior surface of each arm 28A, 28B for engaging the closure mechanism 16. In the exemplary embodiment, the thread starts at the free, proximal end and extends distally along at least a portion of the length of the arms 28A, 28B.

The closure mechanism 16 in the exemplary embodiment is an internal set screw having an external thread that engages the internal thread of the receiver member to capture a spinal fixation element within the recess 30 of the receiver member and, when fully tightened, to fix the spinal fixation element relative to the receiver member 14. Alternatively, the closure mechanism may be dual closure mechanism having an inner and an outer set screw, such as, for example, the Expedium Dual Innie Polyaxial Screw available from DePuy Spine, Inc. of Raynham, Mass. In addition, the closure mechanism may be a non-threaded twist-in cap, such as, for example, the Monarch Typhoon Cap available from DePuy Spine, Inc. of Raynham, Mass., and described in U.S. Pat. No. 6,755,829, incorporated herein by reference.

The exemplary bone anchor assembly 10 may be used with a spinal fixation element such as a rigid spinal rod. The spinal rod may be constructed titanium, titanium alloys, stainless steel, cobalt chrome, PEEK, or other materials suitable for rigid fixation. Alternatively, the spinal fixation element may be a dynamic stabilization member that allows controlled mobility between the instrumented vertebrae.

The exemplary bone anchor assembly is a rigid polyaxial screw in which the bone anchor 12 is fixed, rather than mobile, when the spinal fixation element is fixed to the receiver member 14 of the bone anchor assembly. The spinal fixation element may either directly contact the proximal head 18 of the bone anchor 12 or may contact an intermediate element, e.g., a compression member 100, interposed between the spinal fixation element and the proximal head 18 of the bone anchor 12 to compress the distal outer surface of the proximal head 18 into direct, fixed engagement with the distal inner surface of the receiver member 18 when the spinal fixation element is fixed to the receiver member 16 of the bone anchor assembly by the closure mechanism. In alternative embodiments, the bone anchor assembly may be a mobile screw in which the proximal head 18 of the bone anchor 12 can move relative to the receiver member 14 when the spinal fixation element is fixed to the receiver member 14. An exemplary mobile polyaxial screw is described is U.S. Patent Application Publication No. U.S. 2011-0093021, which is hereby incorporated herein by reference. Alternatively, the bone anchor assembly may be a monoaxial screw, a favored angle screw or a uniplanar screw.

Referring to FIGS. 3 and 4, the distal shaft 20 may be threaded to improve fixation of the bone anchor 12 in bone, such as the pedicle or lateral mass of a vertebra, and, in particular, to facilitate starting the bone anchor 20 in the proximal surface of the bone. In the exemplary embodiment, the distal shaft 20 has a first threaded section 50 distal to the proximal head 18, a second threaded section 52 distal to and adjacent the first threaded section 50, and a third threaded section 54 distal to and adjacent the second threaded section 52. The first threaded section has a first major diameter 56, a first minor diameter 58, and a first length 60. The first major diameter 56 and the first minor diameter 58, in the exemplary embodiment, are constant over the complete first length 60 of the first threaded section 50. The second threaded section 52 has a second major diameter 62, a second minor diameter 64, and a second length 66. In the exemplary embodiment, the second major diameter 62 and the second minor diameter 64 taper in a proximal to distal direction over the complete second length 66 of the second threaded section 52. The second major diameter 62 and the second minor diameter 64 may be less than the first major diameter 56 and the first minor diameter 58 over the complete second length 66 of the second threaded section 52. The third threaded section 54 has a third major diameter 68, a third minor diameter 70, and a third length 72. In the exemplary embodiment, the third major diameter 68 tapers in a proximal to distal direction over the complete third length 72 of the third threaded section 54 and the third major diameter 68 is less than the second major diameter 62 over the complete third length 72 of the third threaded section 54. The third minor diameter 70 may be constant over the complete third length 72 of the third section 54 and the third minor diameter may be equal to the second minor diameter 70 at a transition from the second threaded section 52 to the third threaded section 54.

In the exemplary embodiment, the distal shaft 20 includes an unthreaded distal tip 80 distal to and adjacent to the third threaded section 54. The unthreaded tip 80 may taper in a proximal to distal direction and may be generally conical in shape. In the exemplary embodiment, the angle of the cone 82 formed by the unthreaded tip 80 is approximately 70°. The unthreaded tip is provided to minimize sharp edges, particularly from the thread, at the tip and thereby minimize soft tissue damage during delivery of the bone anchor to the bone surface. The axial length of the unthreaded distal tip 80 is preferably minimized in order to provide the thread as far distally on the shaft as possible.

The tapering minor diameter 64 in the second threaded section 52 and the tapering major diameters 62 and 68 in the second threaded section 52 and third threaded section 54, respectively, facilitate starting of the bone anchor in bone. Moreover, the exemplary thread form eliminates the need for a cutting flute on the distal end on the distal shaft 20. To prevent collapse of the cannula 40 during insertion, a minimum wall thickness in the third section 54 and unthreaded section 80 is preferably maintained. The minimum wall thickness, i.e., the difference between the minor diameter 70 and the diameter of the cannula 40, is preferably greater than 0.5 mm. The minor diameter 64 of the second section 52 preferably tapers until the desired minimum wall thickness is obtained. At this point along the axial length of the distal shaft 20, the second threaded section 52 transitions to the third threaded section 54 and the minor diameter 70 remains constant.

FIGS. 5-7 illustrate another exemplary embodiment of a bone anchor assembly 100 in which the bone anchor 112 is a two-piece construction permitting the distal shaft 120 of the bone anchor 112 to be assembled through the opening in the distal surface 34 of the receiver member 14. In the exemplary embodiment, the bone anchor 112 includes a threaded distal shaft 120 having an analogous thread form to the thread form of the distal shaft 20 of the bone anchor 12 described above. The proximal head of the bone anchor 112 includes two separable components: a cylindrically shaped, non-threaded proximal section 102 at the proximal end of the distal shaft 120 and a resiliently compressible, spherically-shaped retaining member 104 that accepts and retains the proximal section 102 within the retaining member 104. The proximal section 102 includes an annular projection or rib 106 configured to seat within a complementary shaped annular groove 108 provided on the inner surface of the retaining member 104. During assembly, retaining member 104 is positioned within the receiver member 14. The retaining member 104 can be compressed to facilitate positioning in the receiver member 14 after which the retaining member 104 returns to its nominal configuration. The proximal section 102 is inserted through the opening in the distal end surface 34 and into the retaining member 104. The annular projection 106 is seated within the annular groove 108 to retain the proximal section 102 within the retaining member 104, and, thus, the receiver member 14.

FIGS. 8-10 illustrate another exemplary embodiment of a bone anchor assembly 200, in which the bone anchor 212 is configured to facilitate engagement of the bone anchor in bone. In the exemplary embodiment, the first threaded section 250 of the distal shaft 220 of the bone anchor 212 includes distal threaded section 204 and a proximal threaded section 202. The distal threaded section 204, the proximal threaded section 202, and the second threaded section 52, and third threaded section 54 of the distal shaft 220 of the bone anchor 212 may be configured to increase fixation of the bone anchor assembly 10 in bone. The distal threaded section 204 may have a first pitch and a first number of thread starts and the proximal threaded section 202 may have a second pitch less than the first pitch and a second number of thread starts greater than the first number of thread starts. The distal threaded section 204 and the proximal threaded section 202 may have a constant lead.

For a bone anchor assembly designed to be implanted through the pedicle of a vertebra, for example, the threaded distal section 204, and the second threaded section 52 and the third threaded section 54, may be configured to engage the cancellous bone in the anterior vertebral body of the vertebra and the threaded proximal section 202 may be configured to engage the cortical bone of the pedicle of the vertebra. In particular, the threaded distal section 204, and the second threaded section 52 and third threaded section 54, may have a pitch that is greater than (i.e., more coarse) the pitch of the proximal section 202. In the exemplary embodiment, the threaded distal section 204, the second threaded section 52 and third threaded section 54 have the same pitch.

To facilitate insertion of the bone anchor 212 into the vertebra and prevent stripping of the pedicle wall, the distal shaft 220, including the threaded proximal section 202, threaded distal section 204, the second threaded section 52 and third threaded section 54, can have a constant thread lead. The lead of a thread is the distance the distal shaft 220 travels in a direction parallel to the longitudinal axis of the shaft when the distal shaft 220 is rotated one turn (360°). The lead of a thread is equal to the number of thread starts multiplied by the pitch of the thread. As the threaded distal section 204, the second threaded section 52, and the third threaded section 54 have a different pitch than the threaded proximal section 202, the threaded distal section 204, the second threaded section 52, and the third threaded section 54 must have a different number of thread starts than the threaded proximal section 202 in order to have a constant or equal lead. In the exemplary polyaxial bone anchor assembly 200, for example, the lead of the distal shaft 220 is 6 mm, the pitch of distal threaded section 204, the second threaded section 52, and the third threaded section 54 is 3 mm and the distal threaded section 204, the second threaded section 52, and the third threaded section 54 have two thread starts (i.e., the distal threaded section 204, the second threaded section 52, and the third threaded section 54 is dual threaded) and the pitch of proximal threaded section 24 is 1.5 mm and the proximal threaded section 202 has four thread starts (i.e., the proximal threaded section 24 is quad threaded). Further exemplary bone anchors having a thread form for increased bone fixation are disclosed in U.S. patent application Ser. No. 13/110,378, filed May 18, 2011, which is incorporated herein by reference.

The lead of the threaded distal section 204, the second threaded section 52, the third threaded section 54, and the threaded proximal section 24 can vary depending on, for example, the type of bone anchor assembly (e.g., polyaxial, monoaxial, uniplanar) and the vertebra or other bone in which the assembly is to be implanted. For polyaxial bone anchors designed to be inserted through the pedicle of a lumbar or thoracic vertebra, for example, the lead may be from 4 mm to 8 mm and the pitch of the distal threaded section 204, the second threaded section 52, and the third threaded section 54, may be from 2 mm to 4 mm, and the pitch of the proximal threaded section 202 may be from 1 mm to 3 mm. In monoaxial screws, for example, the lead may be 2 mm to 4 mm.

The axial length (i.e., the length in a direction parallel to the longitudinal axis of the distal shaft 220) of the proximal threaded section 202 of the distal shaft 220 can vary depending on the vertebra or other bone in which the assembly is to be implanted and may be selected to correspond to the length of bone the proximal threaded section 202 will engage. For bone anchors designed to be inserted through the pedicle of a lumbar or thoracic vertebra, the axial length of the proximal threaded section 202 may be selected to approximate the length of the pedicle including the distance from the posterior surface of the vertebra through the pedicle to the junction of the pedicle and the anterior vertebral body of the vertebra. In such bone anchors, the axial length of the proximal threaded section 202 may be between 14 mm and 26 mm and preferably is 20 mm. The axial length of the distal shaft 220 may also vary depending on the bone in which the bone anchor 212 is to be inserted. For bone anchors designed to be inserted through the pedicle of a lumbar or thoracic vertebra, the axial length 260 of the distal shaft 220 may be between 20 mm and 100 mm. For bone anchors designed to be inserted through the iliac, the axial length 260 of the distal shaft 220 may be between 60 mm and 150 mm.

The major diameter and the minor diameter of the proximal threaded section 202 and the distal threaded section 204 may be selected based on the bone in which the bone anchor 212 is to be inserted. For bone anchors designed to be inserted through the pedicle of a lumbar or thoracic vertebra (such as the exemplary bone anchor 212), for example, the major diameter of the distal threaded section 204 and the proximal threaded section 202 may be between 4 mm and 10 mm. In the exemplary embodiment, the major diameter of the distal threaded section 204 and the major diameter of the proximal threaded section 202 are equal and constant over the axial length of the distal threaded section 204 and the proximal threaded section 202. In certain exemplary embodiments, the minor diameter of the distal threaded section 204 and the minor diameter of the proximal threaded section 202 are equal and constant over the axial length of the distal threaded section 204 and the proximal threaded section 202. In other exemplary embodiments, the minor diameter of the proximal threaded section 202 is greater than the minor diameter of the distal threaded section 204. The increased minor diameter of the proximal threaded section 202 provides reduced thread depth for the proximal threaded section 202 which increases bone purchase by compressing the bone of the pedicle of the vertebra.

The distal shaft 220 may also include one or more side wall openings 211 or fenestrations that communicate with the cannula 40 to permit bone in-growth or to permit the dispensing of bone cement or other materials through the bone anchor assembly 200. The side wall openings 211 extend radially from the cannula 40 through the side wall of the distal shaft 220. Exemplary systems for delivering bone cement to the bone anchor assembly 200 and alternative bone anchor configurations for facilitating cement delivery are described in U.S. Patent Application Publication No. 2010/0114174, which is hereby incorporated herein by reference. The distal shaft 220 of the bone anchor 212 may also be coated with materials to permit bone growth, such as, for example, hydroxyl apatite, and the bone anchor assembly 200 may be coated all or in-part with anti-infective materials, such as, for example, tryclosan.

While the devices and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed:

1. A bone anchor assembly comprising:
a bone anchor having a proximal head and a distal shaft configured to engage bone, the distal shaft having a first threaded section distal to the proximal head, a second threaded section distal to and adjacent the first threaded section, and a third threaded section distal to and adjacent the second threaded section, the bone anchor including a central passage extending from the proximal head through the distal shaft,
the first threaded section having a first major diameter, a first minor diameter, and a first length, the first major diameter and the first minor diameter being constant over the first length of the first threaded section,
the second threaded section having a second major diameter, a second minor diameter, and a second length, the second major diameter and the second minor diameter tapering in a proximal to distal direction over the second length of the second threaded section, the second major diameter and the second minor diameter being less than the first major diameter and the first minor diameter respectively over the second length of the second threaded section,
the third threaded section having a third major diameter, a third minor diameter, and a third length, the third major diameter tapering in a proximal to distal direction over the third length of the third threaded section, the third major diameter being less than the second major diameter over the third length of the third threaded section, the third minor diameter being constant over the third length of the third section, the third minor diameter being equal to the second minor diameter at a transition from the second threaded section to the third threaded section,
a receiver member for receiving a spinal fixation element to be coupled to the bone anchor, the receiver member having
a proximal end having a pair of spaced apart arms defining a recess therebetween,
a distal end having a distal end surface defining an opening through which at least a portion of the bone anchor extends, and
a closure mechanism positionable between and engaging the spaced apart arms to capture the spinal fixation element within the receiver member and fix the spinal fixation element with respect to the receiver member.

2. The bone anchor assembly of claim 1, wherein the first threaded section includes a distal threaded section and a proximal threaded section, the distal threaded section having a first pitch, the proximal threaded section having a second pitch which is less than the first pitch.

3. The bone anchor assembly of claim 2, wherein the second threaded section has a pitch and the third threaded section has a pitch, wherein the pitch of the second threaded section and the pitch of the third threaded section is are equal to the second pitch.

4. The bone anchor assembly of claim 3, wherein the distal threaded section of the first threaded section has a first number of thread starts and the proximal threaded section of the first threaded section has a second number of thread starts which is greater than the first number of thread starts and wherein the distal threaded section and the proximal threaded section have a constant lead.

5. The bone anchor assembly of claim 4, wherein the second threaded section has a number of thread starts and the third threaded section has a number of thread starts, wherein the number of thread starts of the second threaded section and the number of thread starts of the third threaded section is are equal to the first number of thread starts and wherein the distal threaded section, the proximal threaded section, the second threaded section, and the third threaded section have a constant lead.

6. The bone anchor assembly of claim 1, wherein the distal shaft includes a plurality of side wall openings that communicate with the central passage.

7. The bone anchor assembly of claim 6, wherein the plurality of side wall openings extend radially from the central passage through a side wall of the distal shaft.

8. The bone anchor assembly of claim 1, wherein the bone anchor is pivotable relative to the receiver member prior to fixation of the spinal fixation element to the receiver member.

9. The bone anchor assembly of claim 1, wherein the bone anchor is fixed relative to the receiver member.

10. The bone anchor assembly of claim 1, wherein the distal shaft includes an unthreaded distal tip distal to and adjacent to the third threaded section.

11. The bone anchor assembly of claim 10, wherein the unthreaded distal tip tapers in a proximal to distal direction and is generally conical in shape.

12. A bone anchor assembly comprising:
 a bone anchor having a proximal head and a distal shaft configured to engage bone, the distal shaft having a first threaded section distal to the proximal head, a second threaded section distal to and adjacent the first threaded section, and a third threaded section distal to and adjacent the second threaded section, the bone anchor including a central passage extending from the proximal head through the distal shaft,
 the first threaded section having a first major diameter, a first minor diameter, and a first length, the first major diameter and the first minor diameter being constant over the first length of the first threaded section,
 the second threaded section having a second major diameter, a second minor diameter, and a second length, the second major diameter and the second minor diameter tapering in a proximal to distal direction over the second length of the second threaded section, the second major diameter and the second minor diameter being less than the first major diameter and the first minor diameter respectively over the second length of the second threaded section,
 the third threaded section having a third major diameter, a third minor diameter, and a third length, the third major diameter tapering in a proximal to distal direction over the third length of the third threaded section, the third major diameter being less than the second major diameter over the third length of the third threaded section, the third minor diameter being constant over the third length of the third section, the third minor diameter being equal to the second minor diameter at a transition from the second threaded section to the third threaded section, the central passage having a constant diameter through the first threaded section, second threaded section, and third threaded section,
 a receiver member for receiving a spinal fixation element to be coupled to the bone anchor, the receiver member having
 a proximal end having a pair of spaced apart arms defining a recess therebetween,
 a distal end having a distal end surface defining an opening through which at least a portion of the bone anchor extends, and
 a closure mechanism positionable between and engaging the spaced apart arms to capture the spinal fixation element within the receiver member and fix the spinal fixation element with respect to the receiver member.

\* \* \* \* \*